US008871979B2

(12) United States Patent
Mitchell et al.

(10) Patent No.: US 8,871,979 B2
(45) Date of Patent: Oct. 28, 2014

(54) PROCESS FOR THE PRODUCTION OF METHYLENE-BRIDGED POLYPHENYL POLYAMINES

(75) Inventors: Christopher John Mitchell, Everberg (BE); Avelino Corma Canos, Valencia (ES); Robert Henry Carr, Bertem (BE); Pablo Botella Asuncion, Valencia (ES)

(73) Assignee: Huntsman International LLC, The Woodlands, TX (US)

( * ) Notice: Subject to any disclaimer, the term of this patent is extended or adjusted under 35 U.S.C. 154(b) by 0 days.

(21) Appl. No.: 13/133,410

(22) PCT Filed: Nov. 26, 2009

(86) PCT No.: PCT/EP2009/065863
§ 371 (c)(1),
(2), (4) Date: Jun. 27, 2011

(87) PCT Pub. No.: WO2010/072504
PCT Pub. Date: Jul. 1, 2010

(65) Prior Publication Data
US 2011/0282099 A1 Nov. 17, 2011

(30) Foreign Application Priority Data
Dec. 22, 2008 (EP) .................................. 08172566

(51) Int. Cl.
C07C 211/00 (2006.01)
C07C 209/60 (2006.01)
C07C 209/78 (2006.01)

(52) U.S. Cl.
CPC ............. *C07C 209/60* (2013.01); *C07C 209/78* (2013.01)
USPC ........................................................ 564/330

(58) Field of Classification Search
CPC combination set(s) only.
See application file for complete search history.

(56) References Cited

U.S. PATENT DOCUMENTS

| 4,039,580 A | 8/1977 | Frulla et al. |
| 4,039,581 A | 8/1977 | Frulla et al. |
| 4,554,378 A | 11/1985 | Nafziger et al. |
| 5,241,119 A | 8/1993 | Clerici et al. |
| 6,380,433 B1 | 4/2002 | Perego et al. |
| 6,410,789 B1 | 6/2002 | Becker et al. |
| 7,238,840 B2 | 7/2007 | Botella Asuncion et al. |
| 2003/0023116 A1 | 1/2003 | Klein et al. |
| 2003/0171619 A1 | 9/2003 | Perego et al. |
| 2005/0101801 A1 | 5/2005 | Botella Asuncion et al. |
| 2006/0287555 A1 | 12/2006 | Hagen et al. |

FOREIGN PATENT DOCUMENTS

| BE | 1 013 456 A | 2/2002 |
| EP | 0 329 367 A | 8/1989 |
| WO | WO 01/74755 A | 10/2001 |

OTHER PUBLICATIONS

S. Fukuoka, et al.; "Isocyanate without phosgene"; Chem. Tech.; Nov. 1984; p. 670-676.
Moore, William M.; "Methylenedianiline"; Kirk Othmer, 3rd Edition; vol. II; p. 338-348, 1978.
C. Perego et al.; "Amorphous aluminosilicate catalysts for hydroxyalkylation of aniline and phenol"; Applied Catalysis A; General, 307 (2006); p. 128-136.
A. Corma et al.; "Replacing HCl by solid acids in industrial processes: synthesis of diamino diphenyl mathane (DADPM) for producing polyurethanes"; Chem.Comm. (2004); p. 2008-2010.
A. De Angelis et al.; "Solid Acid Catalysts for Industrial Condensations of Ketones and Aldehydes with Aromatics"; Industrial & Engineering Chemistry Research; 43(5); 2004; p. 1169-1178.

*Primary Examiner* — Clinton Brooks
(74) *Attorney, Agent, or Firm* — Robert A. Diaz

(57) ABSTRACT

A process for providing methylene-bridged polyphenyl polyamines from aniline and formaldehyde according to the invention comprises the subsequent steps of a) condensing aniline and formaldehyde; b) reacting, in a first catalytic reaction step, said condensate over a solid catalyst, whereby an intermediate mixture is provided; c) converting, in a subsequent catalytic reaction step, said intermediate mixture into methylene-bridged polyphenyl polyamines in presence of a subsequent solid catalyst, thereby providing said methylene-bridged polyphenyl polyamines.

9 Claims, No Drawings

PROCESS FOR THE PRODUCTION OF METHYLENE-BRIDGED POLYPHENYL POLYAMINES

CROSS-REFERENCE TO RELATED APPLICATIONS

This application is the National Phase of International Application PCT/EP2009/065863 filed Nov. 26, 2009 which designated the U.S. and which claims priority to EP App. Serial No. 08172566.5 filed Dec. 22, 2008. The noted applications are incorporated herein by reference.

The present invention relates to processes for the production of methylene-bridged polyphenyl polyamines, such as diaminodiphenylmethane isomers, and higher homologues or higher polymers thereof, in particular 4,4'-diaminodiphenylmethane, 2,4'-diaminodiphenylmethane and/or 2,2'-diaminodiphenylmethane. The processes apply a catalytic reaction, and use aniline and formaldehyde as base products.

Diaminodiphenylmethane (MDA) is an intermediate for the preparation of epoxy resins, as well as for the preparation of diphenylmethane diisocyanate (MDI) which, in turn, is a reagent for the production of polymers based on urethane/urea. Diaminodiphenylmethane, and more in general methylene-bridged polyphenyl polyamines, are typically prepared from aniline, or from aniline derivatives, by reacting them with formaldehyde in the presence of a solution of a strong acid such as, for example, hydrochloric, sulfuric or phosphoric acid. Literary sources which describe this type of synthesis are: J. Am. Chem. Soc. 57, 888, 1975; Chem. Tech., November 1984, 670; Kirk Othmer, Vol. II, 3<rd>Edition, 338-348.

To reduce the disadvantages of the strong acids used during the process, several catalysts have been suggested to catalyse the reaction of the condensate of aniline and formaldehyde, also referred to as aminal, to methylene-bridged polyphenyl polyamines. Some catalysts, such as diatomaceous earth, clay or zeolites were suggested, but suffer from an insufficient activity or too short service times, as is set out in U.S. Pat. No. 6,410,789.

The use of different zeolites in a one step reaction for production of methylene-bridged polyphenyl polyamine, more particularly MDA, is disclosed in U.S. Pat. No. 6,380,433.

In U.S. Pat. No. 4,039,580, a two step process is described, wherein dewatered condensate, provided by condensation of aniline and formaldehyde, is first reacted into amino benzyl amines by a first catalyzed reaction, after which it is further reacted into methylene-bridged polyphenyl polyamine. The catalysts for both catalytic reactions are diatomaceous earths, clays or zeolites.

Further, during conversion of aminal to MDA, a side reaction occurs, forming so-called N-methylated MDA. The N-methylated groups cannot be transformed into isocyanates, and hence may negatively affect the provision of polyurethane or polyurea, when reacting poly- or diisocyanates with isocyanate-reactive compounds.

The selectivity of several catalysts, suitable to provide methylene-bridged polyphenyl polyamine, and their tendency to catalyze the conversion of aminal to N-methylated MDA, is described in "Amorphous aluminosilicate catalysts for hydroxylation of aniline and phenol" from C. Perego et al. published in Applied Catalysis A: general 307 (2006) 128-136. Also the document "Replacing HCl by solid acids in the industrial processes: synthesis of diamino diphenyl methane (DADPM) for producing polyurethanes", from A. Corma et al., chemical communication 2004, page 2008-2010, describes these features for different suitable catalysts.

A further requirement of the catalysts when used in industrial processes, is their service life and life time. Catalysts typically have the tendency to clog or deactivate over time. Cleaning of the catalyst bed is required to recover the catalyst. Such cleaning requires the process to be shut down or at least the catalyst bed to be taken out of the process flow. Such maintenance causes not only additional work and costs, but also may cause wear to the catalyst bed and may cause yield losses.

It is the subject of the present invention to provide a process or method to provide methylene-bridged polyphenyl polyamines, in particular diaminodiphenylmethane isomers, and higher homologues thereof or higher polymers thereof, which provide a longer life time and service life to the catalyst bed or beds used. It is the subject of the present invention to provide a process or method to provide methylene-bridged polyphenyl polyamines, in particular diaminodiphenylmethane isomers, and higher homologues thereof or higher polymers thereof, which require less maintenance interventions for cleaning the catalyst bed or beds.

Some processes according to the present invention have the advantage that a diamine content in the provided methylene-bridged polyphenyl polyamines in the range of 30% w to 85% w may be obtained. In the preferred case of diaminodiphenylmethane (MDA), the total amount of 4,4'-MDA may be preferably in the range of more than 75% w, the w % being over the total weight of total diamines present.

Some processes according to the present invention have the advantage that the process can be run using relatively low amounts of aniline as compared to the amount of formaldehyde, i.e. which can be run with low molar ratio of aniline to formaldehyde (hereinafter referred to as mol ratio A/F) for providing the condensate. Some processes according to the present invention have the advantage that the process does not necessarily require changing the initial A/F, as used to provide the condensate, throughout the entire process. Some processes according to the present invention have the advantage that a low total amount of N-methyl groups may be generated in the provided methylene-bridged polyphenyl polyamines.

Some or all of these advantages can be obtained by using a process according the present invention.

According to a first aspect of the present invention, a process for providing methylene-bridged polyphenyl polyamines from aniline and formaldehyde according to the present invention comprises the subsequent steps of a) condensing aniline and formaldehyde, providing a condensate;

b) reacting, in a first catalytic reaction step, said condensate over a solid catalyst being chosen from the group consisting of clays, silicates, silica-aluminas and ion exchange resins, whereby an intermediate mixture is provided, the intermediate mixture comprising amino benzyl amines;

c) converting, in a subsequent catalytic reaction step, said intermediate mixture into methylene-bridged polyphenyl polyamines in presence of a subsequent solid catalyst being chosen from the group consisting of zeolites, delaminated zeolites and ordered mesoporous materials, thereby providing said methylene-bridged polyphenyl polyamines.

The term "methylene-bridged polyphenyl polyamines" includes both diaminodiphenylmethane isomers, and higher homologues thereof or higher polymers thereof. The process in particular is suitable to provide diaminodiphenylmethane isomers such as 4,4'- diaminodiphenylmethane, 2,4'-diaminodiphenylmethane and/or 2,2'-diaminodiphenylmethane.

Condensing aniline and formaldehyde and converting the condensate, also referred to as neutral condensate and often called "aminal", can be executed in one and the same step, but are preferably two distinct, consecutive steps.

The condensing of the aniline and formaldehyde is preferably obtained by reaction of aniline and formaldehyde in the absence of a catalyst at a reaction temperature within the range of about 30° C. to about 100° C. After reaction has completed, the excess water may be removed by a variety of means such as physical separation, distillation etc. The molar ratio of aniline to formaldehyde, i.e. the mol ratio A/F is chosen in the range of 2 to 3.5, preferably in the range of 2.5 to 3.5, such as in the range of 2.5 to 3.2, e.g. in the range of 2.5 to 3.

In general, it was found that the lower the A/F ratio used, the more higher molecular weight species being formed. As progressively larger amounts of aniline are used, the yield of aminal is progressively increased, whereas the amount of higher molecular weight species decreases.

Formaldehyde may be employed in any of its commercially available forms. Thus, formalin, paraformaldehyde, stabilized methanol solutions of formaldehyde, gas etc., may be employed.

The conditions for the conversion of the condensate into an intermediate mixture include a reaction temperature within the range of about 30° C. to about 100° C. and more preferably within the range of about 30° C. to about 70° C. Pressure is not particularly critical with respect to the process. However, the pressure should be sufficient to provide for liquid phase reaction conditions. Thus, pressures ranging from 0.1 to 5 MPa may preferably be employed.

The conversion of the intermediate mixture into methylene-bridged polyphenyl polyamines, such as diaminodiphenylmethane isomers, and higher homologues thereof or higher polymers, according to the present invention, is carried out by reaction of the intermediate mixture over one or more catalysts, with a reaction temperature within the range of about 70° C. to about 250° C., and more preferably within the range of about 100° C. to about 200° C. The reaction temperature is higher than used for the conversion of the condensate. Pressure is not particularly critical with respect to the process. However, the pressure should be sufficient to provide for liquid phase reaction conditions. Thus, pressures ranging from 0.1 to 5 MPa may be employed.

According to some embodiments of the present invention, the catalyst used in the first catalytic reaction step for providing the intermediate mixtures may be chosen from the group consisting of sheet silicate material and clays.

Examples of such preferred materials include kaolinites, montmorillonites, hectorites, sepiolites and attapulgites.

The catalytic reaction as referred to in step b) is to transfer the condensate into amino benzyl amines, such as 2-aminobenzylaniline and 4-aminobenzylaniline (also known as 2-ABA, respectively 4-ABA) and higher homologues.

The conversion of condensate into the intermediate mixture comprising amino benzyl amines, is preferably run such that at least 90% w of the aminal from the neutral condensate is converted into amino benzyl amines. Preferably 70% w of the intermediate mixture are amino benzyl amines.

The intermediate mixture preferably comprises only up to 0.5% w of N-methylated substances.

The intermediate mixture preferably comprises only up to 20% w of methylene-bridged polyphenyl polyamines, such as 4,4'-diaminodiphenylmethane, 2,4'-diaminodiphenylmethane and/or 2,2'-diaminodiphenylmethane.

The conversion of the condensate into an intermediate mixture may be carried out batch-wise, semi-continuously or continuously. Preferably fixed bed reactors may be employed. The form of the catalyst particles may be varied according to the preferred reactor configuration, and may include micro-spheroidal particles, granules, extrudates, pellets etc. The reaction may also be carried out using one or more reactor and catalyst types in combination.

The formed catalysts may include a binder, such as silica, silica-alumina and alumina. For the preferred fixed bed reactor configuration, the weight hourly space velocity (WHSV) for the conversion of condensate to the intermediate mixture may preferably be in the range of 0.1 to 10 per hour. Weight hourly space velocity (WHSV) is the mass flow per hour per unit mass of catalyst.

In the second catalytic step, preferably, the solid catalyst used in the conversion of the intermediate mixtures into methylene-bridged polyphenyl polyamines is a zeolite, a delaminated zeolite or an ordered mesoporous material. According to some embodiments of the present invention, the subsequent catalyst may be chosen from the group consisting of zeolite Beta, delaminated zeolite ITQ2, delaminated zeolite ITQ18 and the ordered mesoporous material MCM-41.

The catalyst used for the conversion of the intermediate mixture into methylene-bridged polyphenyl polyamines, such as diaminodiphenylmethane isomers, and higher homologues thereof or higher polymers preferably is a catalyst from the group of a variety of heterogeneous acid catalysts, including zeolites, delaminated zeolites and ordered mesoporous materials. Examples of zeolites which can be used within the scope of the present invention include mordenite, faujasite, Y zeolite, MCM22, ERB-1 and Beta. Examples of delaminated zeolites which can be used are ITQ2, ITQ6, ITQ18 and ITQ20. The class of ordered mesoporous materials includes MCM-41, MCM-48, SBA-15 and MCM-56. Preferred catalysts are zeolite Beta and delaminated zeolites ITQ2 and ITQ18, and the ordered mesoporous material MCM-41.

The reaction of the intermediate mixture into methylene-bridged polyphenyl polyamines, such as diaminodiphenylmethane isomers, and higher homologues thereof or higher polymers, according to the present invention, may be carried out batch-wise, semi-continuously or continuously. Preferably fixed bed reactors may be employed. The form of the catalyst particles may be varied according to the preferred reactor configuration, and may include micro-spheroidal particles, granules, extrudates, pellets etc. The reaction may also be carried out using one or more reactor and catalyst types in combination. The formed catalysts may include a binder, such as silica, silica-alumina and alumina. For the preferred fixed bed reactor configuration, the weight hourly space velocity (WHSV) for the conversion of the intermediate mixture to methylene bridged polyphenyl polyamines over a fixed bed reactor may preferably be in the range of 0.1 to 10 per hour. Weight hourly space velocity (WHSV) is the mass flow per hour per unit mass of catalyst.

The conversion of the intermediate mixture comprising amino benzyl amines into methylene-bridged polyphenyl polyamines, is preferably run such that at least 99 w% of the amino benzyl amines from the intermediate mixture is converted into methylene-bridged polyphenyl polyamines. When diaminodiphenylmethane isomers such as 4,4'-diaminodiphenylmethane, 2,4'-diaminodiphenylmethane and/or 2,2'-diaminodiphenylmethane are to be provided, preferably 50 to 80% w of the methylene-bridged polyphenyl polyamines are 4,4'-diaminodiphenylmethane, 2,4'-diaminodiphenylmethane or 2,2'-diaminodiphenylmethane. More preferred, at least 60% w of the methylene-bridged polyphenyl polyamines are 4,4'-diaminodiphenylmethane.

The methylene-bridged polyphenyl polyamines preferably comprises only up to 0.5% w of N-methylated compounds.

This subsequent catalytic reaction converts these amino benzyl amines into methylene-bridged polyphenyl polyamines, such as e.g. diaminodiphenylmethane isomers such as 4,4'-diaminodiphenylmethane (also known as 4,4'-MDA or p,p'-MDA), 2,4'-diaminodiphenylmethane (also known as 2,4'-MDA or o,p'-MDA) and/or 2,2'-diaminodiphenylmethane (also known as 2,2'-MDA or o,o'-MDA). These methylene-bridged polyphenyl polyamines, such as e.g. diaminodiphenylmethane, may be used to provide di- or polyisocyanates, by phosgenation of the methylene-bridged polyphenyl polyamines.

The concentration of diaminodiphenylmethane isomers such as 4,4'-diaminodiphenylmethane, 2,4' -diaminodiphenylmethane and/or 2,2'-diaminodiphenylmethane can be determined using standard available analytical equipment and routines, well known in the art.

A side reaction during the process is the formation of compounds comprising N-methyl groups. Though the applicant does not want to be bound by any theory, it is believed that the N-methylated compounds are formed in particular when both amino benzyl amines and aminals are present in the same reaction, the reaction being catalyzed by a solid catalyst.

These N-methylated groups cannot be transformed into isocyanate groups by phosgenation, and their presence in the resulting di- or polyisocyanate disturb the use reaction of the di- or polyisocyanates with reactive groups for providing polyurethane.

The process according to the invention thus includes a two step catalytic conversion of condensate to methylene-bridged polyphenyl polyamines.

Though the reason behind is not clear, it was found that the combination of using a solid catalyst from the group consisting of clays, silicates, silica-aluminas and ion exchange resins, for providing intermediate mixtures comprising amino benzyl amines and thereafter using a subsequent solid catalyst being chosen from the group consisting of zeolites, delaminated zeolites and ordered mesoporous materials, for providing the methylene-bridged polyphenyl polyamines, results in both a reduced amount of N-methylated compounds in the methylene-bridged polyphenyl polyamines, while the life time or service life of the second catalyst can be extended significantly.

The amount of N-methylated compounds in the methylene-bridged polyphenyl polyamines can be determined using $^1$H-NMR.

The N-methylated compounds, is preferably kept within a range of 0.1 to 0.5% w.

An advantage of the provision of two distinct catalytic steps in the process according to the present invention, is that the activity of the catalyst used to convert the intermediate mixture into methylene-bridged polyphenyl polyamines, such as diaminodiphenylmethane isomers, and higher homologues thereof or higher polymers, is significantly increased, when compared to the use of the same catalyst to perform the complete conversion from aniline and formaldehyde to methylene-bridged polyphenyl polyamines, such as diaminodiphenylmethane isomers, and higher homologues thereof or higher polymers. A doubling of the activity could be noticed.

Additionally, the service life of this catalyst is increased, resulting in less process downtime for occasional or structural process maintenance interventions and a more economic use of this catalyst.

The methylene-bridged polyphenyl polyamines of the present invention are useful for a variety of purposes. For example, they may be utilized as raw materials for the production of the corresponding di- and polyisocyanates. They may also be used in the production of polyols, formed via the polymerisation reaction of the diamine and polyamines products of this invention with ethylene oxide or propylene oxide or in epoxy resin systems.

According to a second aspect of the present invention, a reactor suitable to perform a process for providing diaminodiphenylmethane according to the first aspect of the present invention is provided.

According to this aspect of the invention, a reactor for providing methylene-bridged polyphenyl polyamines is provided. The reactor comprises a) a first catalytic reacting system equipped to receive a condensate of aniline and formaldehyde, said first reacting system comprising a solid catalyst being chosen from the group consisting of clays, silicates, silica-aluminas and ion exchange resins, the first catalytic reacting system being fit to react the condensate at a reaction temperature within the range of about 30° C. to about 100° C., over the solid catalyst for providing an intermediate mixture comprising amino benzyl amines;

b) a second catalytic reacting system, equipped to receive the intermediate mixture of the first reacting system, the second catalytic reacting system comprising a solid catalyst being chosen from the group consisting of zeolites, delaminated zeolites and ordered mesoporous materials, the second catalytic reacting system being fit to react the intermediate mixture over the solid catalyst at a temperature within the range of about 70° C. to about 250° C., the reaction temperature in the second catalytic reacting system being higher than the reaction temperature in the first catalytic reacting system, the second catalytic reacting system thereby providing methylene-bridged polyphenyl polyamines.

Each of the reacting systems may be a system comprising one or a plurality of reactor units, each unit comprising one or more tubes filled with the catalyst, which tubes are charged with the products to be reacted in parallel. The tubes may be oriented substantially vertically, and the product flow may be bottom-up or top-bottom.

Each of the reacting systems may comprise a plurality of reactor units being coupled onto the other in series.

In the first reacting system, each reactor unit can be provided with a solid catalyst being chosen from the group consisting of clays, silicates, silica-aluminas and ion exchange resins. The solid catalysts may vary between these reactor units. Alternative or additionally, each reactor unit may comprise a bed having subsequent layers of different solid catalyst.

In the second reacting system, each reactor unit can be provided with a solid catalyst being chosen from the group consisting of zeolites, delaminated zeolites and ordered mesoporous materials. The solid catalysts may vary between these reactor units. As an example, the second reactor system could consist of two reactors with an intermediate heater, the first reactor containing the solid catalyst ITQ18, and the second reactor unit after the heater containing a layer of the solid catalyst ITQ18 followed by a layer of the solid catalyst ITQ2.

Each reactor unit may be an adiabatic reactor unit. Between subsequent adiabatic reactor units, the process liquid may be cooled. This is in particular the case for the first catalytic reacting system, when the first catalytic reacting system comprises two or more serially coupled adiabatic reactor units. Between subsequent adiabatic reactor units, the process liquid may be heated. This is in particular the case for the second catalytic reacting system, when the second catalytic reacting system comprises two or more serially coupled adiabatic reactor units.

The reactor according to the present invention may further comprise a condensing system for condensing aniline and formaldehyde. This condensing system is coupled to the first catalytic reaction system for providing the condensate as influent of this first catalytic reaction system.

The independent and dependent claims set out particular and preferred features of the invention. Features from the dependent claims may be combined with features of the independent or other dependent claims as appropriate.

The above and other characteristics, features and advantages of the present invention will become apparent from the following detailed description. This description is given for the sake of example only, without limiting the scope of the invention.

The present invention will be described with respect to particular embodiments.

It is to be noticed that the term "comprising", used in the claims, should not be interpreted as being restricted to the means listed thereafter; it does not exclude other elements or steps. It is thus to be interpreted as specifying the presence of the stated features, steps or components as referred to, but does not preclude the presence or addition of one or more other features, steps or components, or groups thereof. Thus, the scope of the expression "a device comprising means A and B" should not be limited to devices consisting only of components A and B. It means that with respect to the present invention, the only relevant components of the device are A and B.

Throughout this specification, reference to "one embodiment" or "an embodiment" are made. Such references indicate that a particular feature, described in relation to the embodiment is included in at least one embodiment of the present invention. Thus, appearances of the phrases "in one embodiment" or "in an embodiment" in various places throughout this specification are not necessarily all referring to the same embodiment, though they could. Furthermore, the particular features or characteristics may be combined in any suitable manner in one or more embodiments, as would be apparent to one of ordinary skill in the art from this disclosure.

The following terms are provided solely to aid in the understanding of the invention. Unless otherwise specified, the term "% w" or weight percentage of a component refers to the weight of the component over the total weight of the composition in which the component is present and of which it is part.

The following examples illustrate processes according to the invention. It is understood, that these examples are merely illustrative, and that the invention is not to be limited thereto.

EXAMPLE 1 a) Synthesis of the neutral condensate 4000 ml of aniline was added to a 5 liter oil-heated reactor. Whilst the oil temperature was increased to 60° C., 825 ml of 47% aqueous formalin was added, over a period of 20 minutes with continuous stirring. During the addition of the formalin the temperature increased to around 70° C. Once the formalin addition was completed, the mixture was stirred for a further 30 minutes whilst the temperature dropped to around 55° C. The mixture was allowed to phase separate overnight then the organic (bottom) layer was collected and stored in an oven at 50° C.

b) Converting the condensate into an intermediate mixture in a first catalytic step Neutral condensate was fed for 96 hours at a flow rate of 0.7 ml/min to a 1 inch diameter column packed with 80 g of silica-alumina tablets (Si-1221T, Engelhard), held in an electrically heated furnace at a temperature of 90° C. The so obtained intermediate mixture was collected and stored at 50° C. until required.

c) Conversion of intermediate mixture into methylene-bridged polyphenyl polyamines, in particular into diaminodiphenylmethane by a subsequent catalytic reaction.

The intermediate mixture was fed for a period of 48 hours at a flow rate of 0.7 ml/min to a 1 inch diameter column packed with 42 g of ITQ18 catalyst (1.2 mm diameter extrudates) at a temperature of 125° C. The reaction product, comprising diaminodiphenylmethane, was analysed at intervals by gas chromatography (GC).

Over a 48 hour period the yield of diaminodiphenylmethane as determined by GC analysis declined from 38% w to 31% w. Approximately 82% of the diaminophenylmethane was 4,4'-diaminophenylmethane.

EXAMPLE 2 a) Synthesis of the neutral condensate

Neutral condensate was prepared in the same manner as Example 1.

b) Converting the condensate into an intermediate mixture in a first catalytic step Neutral condensate was fed for 60 hours at a flow rate of 1 ml/min to a 1 inch diameter column packed with 100 g of an acid activated clay (F25, Engelhard), held in an electrically heated furnace at a temperature of 70° C. The intermediate mixture was collected and stored at 50° C. until required.

c) Conversion of intermediate mixture into methylene-bridged polyphenyl polyamines, in particular into diaminodiphenylmethane by a subsequent catalytic reaction. The intermediate mixture was fed for a period of 55 hours at a flow rate of 1 ml/min to a 1 inch diameter column packed with 41 g of ITQ18 catalyst (1.2 mm diameter extrudates) at a temperature of 130° C. The reaction product was analysed at intervals by gas chromatography (GC).

Over a 48 hour period the yield of diaminodiphenylmethane as determined by GC analysis declined marginally from 38% w to 35% w. Approximately 85% of the diaminophenylmethane was 4,4'-diaminophenylmethane.

EXAMPLE 3 a) Synthesis of the neutral condensate

Neutral condensate was prepared in the same manner as Example 1.

b) Converting the condensate into an intermediate mixture in a first catalytic step Neutral condensate was fed for 48 hours at a flow rate of 1 ml/min to a 1 inch diameter column packed with 52 g of an amorphous hydrous aluminosilicate material (T4649, Sud-Chemie), held in an electrically heated furnace at a temperature of 80° C. The intermediate mixture was collected and stored at 50° C. until required.

c) Conversion of intermediate mixture into methylene-bridged polyphenyl polyamines, in particular into diaminodiphenylmethane by a subsequent catalytic reaction.

The intermediate mixture was fed for a period of 48 hours at a flow rate of 1 ml/min to a 1 inch diameter column packed with 42 g of ITQ18 catalyst (1.2 mm diameter extrudates) at a temperature of 125° C. The reaction product was analysed at intervals by gas chromatography (GC).

Over a 48 hour period the yield of diaminodiphenylmethane as determined by GC analysis declined marginally from 41% w to 40% w. Approximately 80% of the diaminophenylmethane was 4,4'- diaminophenylmethane.

EXAMPLE 4 a) Synthesis of the neutral condensate

Neutral condensate was prepared in the same manner as Example 1.

b) Converting the condensate into an intermediate mixture in a first catalytic step Neutral condensate was treated in the same manner as Example 3 c) Conversion of intermediate mixture into methylene-bridged polyphenyl polyamines, in particular into diaminodiphenylmethane by a subsequent catalytic reaction.

The intermediate mixture was fed for a period of 68 hours at a flow rate of 1 ml/min to a 1 inch diameter column packed with 50 g of Zeolite Beta catalyst (CP814, PQ Corporation) at a temperature of 125° C. The reaction product was analysed at intervals by gas chromatography (GC).

Over a 67 hour period the yield of diaminodiphenylmethane as determined by GC analysis declined from 45% w to 43% w. Approximately 68% of the diaminophenylmethane was 4,4'- diaminophenylmethane.

EXAMPLE 5

(Comparative)—Conversion of Condensate into Diaminodiphenylmethane Using One Catalytic Reaction Step a) Synthesis of the neutral condensate Neutral condensate was prepared in the same manner as Example 1.

b) converting condensate into diaminodiphenylmethane comprising reaction product The condensate was fed for a period of 69 hours at a flow rate of 1 ml/min to a 1 inch diameter column packed with 41 g of ITQ18 catalyst (1.2 mm diameter extrudates) at a temperature of 125° C. The reaction product was analysed at intervals by gas chromatography (GC).

Over a 69 hour period the yield of diaminodiphenylmethane as determined by GC analysis declined significantly from 37% w to less than 20% w. Approximately 81% of the diaminophenylmethane was 4,4'-diaminophenylmethane.

EXAMPLE 6

(Comparative)—Conversion of Condensate into Diaminodiphenylmethane Using One Catalytic Reaction Step a) Synthesis of the neutral condensate Neutral condensate was prepared in the same manner as Example 1.

b) converting condensate into diaminodiphenylmethane comprising reaction product The condensate was fed for a period of 68 hours at a flow rate of 1 ml/min to a 1 inch diameter column packed with 50 g of Zeolite Beta catalyst (CP814, PQ Corporation) at a temperature of 125° C. The reaction product was analysed at intervals by gas chromatography (GC).

Over a 68 hour period the yield of diaminodiphenylmethane as determined by GC analysis declined significantly from 41% w to 11% w. Approximately 70% of the diaminophenylmethane was 4,4'-diaminophenylmethane.

It is to be understood that although preferred embodiments and/or materials have been discussed for providing embodiments according to the present invention, various modifications or changes may be made without departing from the scope and spirit of this invention.

The invention claimed is:

1. A process for providing methylene-bridged polyphenyl polyamines from aniline and formaldehyde, wherein the process comprises the subsequent steps of:
   a) condensing aniline and formaldehyde, providing a condensate, the molar ratio of aniline to formaldehyde being chosen in the range of 2 to 3.5;
   b) reacting, in a first catalytic reaction step, at a reaction temperature within the range of about 30° C. to about 100° C., said condensate over silica-alumina whereby an intermediate mixture is provided, the intermediate mixture comprising amino benzyl amines; and
   c) converting in a subsequent catalytic reaction step, at a temperature within the range of about 70° C. to about 250° C. and in the presence of delaminated zeolite ITQ18, said intermediate mixture into methylene-bridged polyphenyl polyamines.

2. A process according to claim 1, wherein the reaction temperature of said first catalytic reaction is about 90° C.

3. A process according to claim 2, wherein the reaction temperature of said subsequent catalytic reaction step ranges from about 125° C. to about 130° C.

4. A process for providing methylene-bridged polyphenyl polyamines from aniline and formaldehyde, wherein the process comprises the subsequent steps of:
   a) condensing aniline and formaldehyde, providing a condensate, the molar ratio of aniline to formaldehyde being chosen in the range of 2 to 3.5;
   b) reacting, in a first catalytic reaction step, at a reaction temperature within the range of about 30° C. to about 100° C., said condensate over activated clay; and
   c) converting in a subsequent catalytic reaction step, at a temperature within the ranqe of about 70° C. to about 250° C. and in the presence of delaminated zeolite ITQ18, said intermediate mixture into methylene-bridqed polyphenyl polyamines.

5. The process according to claim 4, wherein the reaction temperature of said first catalytic reaction is about 70° C.

6. The process according to claim 5, wherein the reaction temperature of said subsequent catalytic reaction step ranges from about 125° C. to about 130° C.

7. A process for providing methylene-bridged polyphenyl polyamines from aniline and formaldehyde, wherein the process comprises the subsequent steps of:
   (a) condensing aniline and formaldehyde, providing a condensate, the molar ratio of aniline to formaldehyde being chosen in the range of 2 to 3.5;
   (b) reacting, in a first catalytic reaction step, at a reaction temperature within the range of about 30° C. to about 100° C., said condensate over amorphous hydrous aluminosilicate; and
   (c) converting in a subsequent catalytic reaction step, at a temperature within the ranqe of about 70° C. to about 250° C. and in the presence of delaminated zeolite ITQ18 or zeolite Beta catalyst (CP814), said intermediate mixture into methylene-bridqed polyphenyl polyamines.

8. The process according to claim 7, wherein the reaction temperature of said catalytic reaction is about 80° C.

9. The process according to claim 8, wherein the reaction temperature of said subsequent catalytic reaction step ranges from about 125° C. to about 130° C.

* * * * *